(12) United States Patent
Haase

(10) Patent No.: US 11,735,303 B2
(45) Date of Patent: Aug. 22, 2023

(54) APPARATUS AND METHOD FOR DETERMINING A COMPOSITION OF A REPLACEMENT THERAPY TREATMENT

(71) Applicant: David Haase, Brentwood, TN (US)

(72) Inventor: David Haase, Brentwood, TN (US)

(73) Assignee: David Haase, Brentwood, TN (US)

( * ) Notice: Subject to any disclaimer, the term of this patent is extended or adjusted under 35 U.S.C. 154(b) by 0 days.

(21) Appl. No.: 17/846,244

(22) Filed: Jun. 22, 2022

(65) Prior Publication Data

US 2022/0406430 A1    Dec. 22, 2022

Related U.S. Application Data

(60) Provisional application No. 63/213,271, filed on Jun. 22, 2021.

(51) Int. Cl.
*G16H 20/10* (2018.01)
*G06N 5/022* (2023.01)
*G16H 10/60* (2018.01)

(52) U.S. Cl.
CPC ............. *G16H 20/10* (2018.01); *G06N 5/022* (2013.01); *G16H 10/60* (2018.01)

(58) Field of Classification Search
CPC ......... G16H 20/10; G16H 10/60; G06N 5/002
See application file for complete search history.

(56) References Cited

U.S. PATENT DOCUMENTS

| 6,010,697 A | 1/2000 | Smith et al. |
| 7,297,539 B2 | 11/2007 | Mandalam et al. |
| 7,410,798 B2 | 8/2008 | Mandalam et al. |

(Continued)

FOREIGN PATENT DOCUMENTS

| CN | 110100812 A | 8/2019 |
| JP | 11023573 A2 | 12/1999 |
| WO | 2003020920 | 3/2003 |

OTHER PUBLICATIONS

Hunt et al, , Oral Bovine Serum Concentrate Improves Cryptosporidial Enteritis in Calves, Dec. 31, 2002.

(Continued)

*Primary Examiner* — Jay M. Patel
(74) *Attorney, Agent, or Firm* — Caldwell Intellectual Property Law

(57) ABSTRACT

An apparatus and method for determining a composition of a replacement therapy treatment is presented, the apparatus at least a processor and a memory communicatively connected to the processor, the memory containing instructions configuring the at least a processor to receive a user input wherein the user input comprises at least an identifier and a constitutional history of the user, generate a first condition descriptor as a function of the user input, determine a composition of a replacement therapy treatment as a function of the first condition descriptor, wherein the determination comprises training a first machine-learning process using user training data, wherein the user training data correlates user inputs to compositions of the replacement therapy treatment and determining the composition as a function of the user input and the first machine learning process, and output the composition of the replacement therapy treatment as a function of the determination.

18 Claims, 6 Drawing Sheets

(56) References Cited

U.S. PATENT DOCUMENTS

| | | |
|---|---|---|
| 7,723,106 B2 | 5/2010 | Hwang et al. |
| 7,932,084 B2 | 4/2011 | Katz et al. |
| 8,415,158 B2 | 4/2013 | Robins et al. |
| 8,762,074 B2 | 6/2014 | Hwang et al. |
| 9,018,010 B2 | 4/2015 | Amit et al. |
| 9,040,297 B2 | 5/2015 | Amit et al. |
| 2006/0275900 A1 | 12/2006 | Presnell et al. |
| 2008/0085557 A1 | 4/2008 | Robins et al. |
| 2010/0183561 A1 | 7/2010 | Sakthivel et al. |
| 2014/0031976 A1* | 1/2014 | Reinhardt ............ G16H 40/60 700/239 |
| 2014/0170748 A1 | 6/2014 | Bhatia et al. |
| 2016/0279315 A1 | 9/2016 | Heide |
| 2017/0199203 A1* | 7/2017 | Britz-McKibbin ........................ G01N 33/6806 |
| 2018/0295834 A1 | 10/2018 | Reid et al. |
| 2020/0222498 A1* | 7/2020 | Chang ................. A61K 38/12 |
| 2020/0356864 A1* | 11/2020 | Neumann ............ G06N 3/088 |
| 2022/0260574 A1* | 8/2022 | Dittamore .......... G01N 33/5011 |

OTHER PUBLICATIONS

Brusow et al., Bovine Milk Immunoglobulins for Passive Immunity to Infantile Rotavirus Gastroenteritis, Dec. 31, 1987.

Hammer et al., Characterization of a Colostrum Replacer and a Colostrum Supplement Containing IgG Concentrate and Growth Factors, Dec. 31, 2004.

* cited by examiner

APPARATUS AND METHOD FOR DETERMINING A COMPOSITION OF A REPLACEMENT THERAPY TREATMENT

CROSS-REFERENCE TO RELATED APPLICATIONS

This application claims the benefit of priority of U.S. Provisional Patent Application Ser. No. 63/213,271, filed on Jun. 22, 2021, and titled "METHODS AND SYSTEMS FOR DETERMINING A COMPOSITION OF A REPLACEMENT THERAPY TREATMENT," which is incorporated by reference herein in its entirety.

FIELD OF THE INVENTION

The present invention generally relates to the field of medicine. In particular, the present invention is directed to an apparatus and method for determining a composition of a replacement therapy treatment.

BACKGROUND

Replacement therapy is widely used to treat many ailments. Most common uses for replacement therapy are the replacing a lost nutrient or substance. For example, hormone replacement therapy is primarily used to treat menopausal effects or osteoporosis by treatment with estrogens or progestogens. Other types of replacement therapies aim at epidermal hydration, skin elasticity, skin thickness, and also reduces skin wrinkles. Implementing such therapies to treat major ailments can be challenging.

SUMMARY OF THE DISCLOSURE

In one aspect, an apparatus for determining a composition of a replacement therapy treatment is presented. The apparatus comprises at least a processor and a memory communicatively connected to the processor, the memory containing instructions configuring the at least a processor to receive a user input wherein the user input comprises at least an identifier and a constitutional history of the user, generate a first condition descriptor as a function of the user input, determine a composition of a replacement therapy treatment as a function of the first condition, wherein the determination comprises training a first machine-learning process using user training data, wherein the user training data correlates user inputs to compositions of the replacement therapy treatment and determining the composition as a function of the user input and the first machine learning process, and output the composition of the replacement therapy treatment as a function of the determination.

In another aspect of the disclosure, a method for determining a composition of a replacement therapy treatment, the method comprises receiving, at a processor, a user input, wherein the user input comprises at least an identifier and a constitutional history of the user, generating, at the computing device, a first condition descriptor as a function of the user input, determining, at a processor, a composition of a replacement therapy treatment as a function of the first condition, wherein the determination comprises training a first machine-learning process using user training data, wherein the user training data correlates user inputs to compositions of the replacement therapy treatment and determining the composition as a function of the user input and the first machine learning process, and outputting, at a processor, the composition of the replacement therapy treatment as a function of the determination.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to an apparatus and method for determining a composition of a replacement therapy treatment. The apparatus comprises at least a processor and a memory communicatively connected to the processor, the memory containing instructions configuring the at least a processor to perform the steps described herein. The processor may receive a user input wherein the user input comprises at least an identifier and a constitutional history of the user. The apparatus may also generate a first condition descriptor as a function of the user input. Aspects of the present disclosure may also include determining a composition of a replacement therapy treatment as a function of the first condition descriptor wherein the determination comprises training a first machine-learning process using user training data wherein the user training data correlates user inputs to compositions of the replacement therapy treatment and determining the composition as a function of the user input and the first machine learning process. The system may also include outputting the composition of the replacement therapy treatment as a function of the determination.

Figure 1:
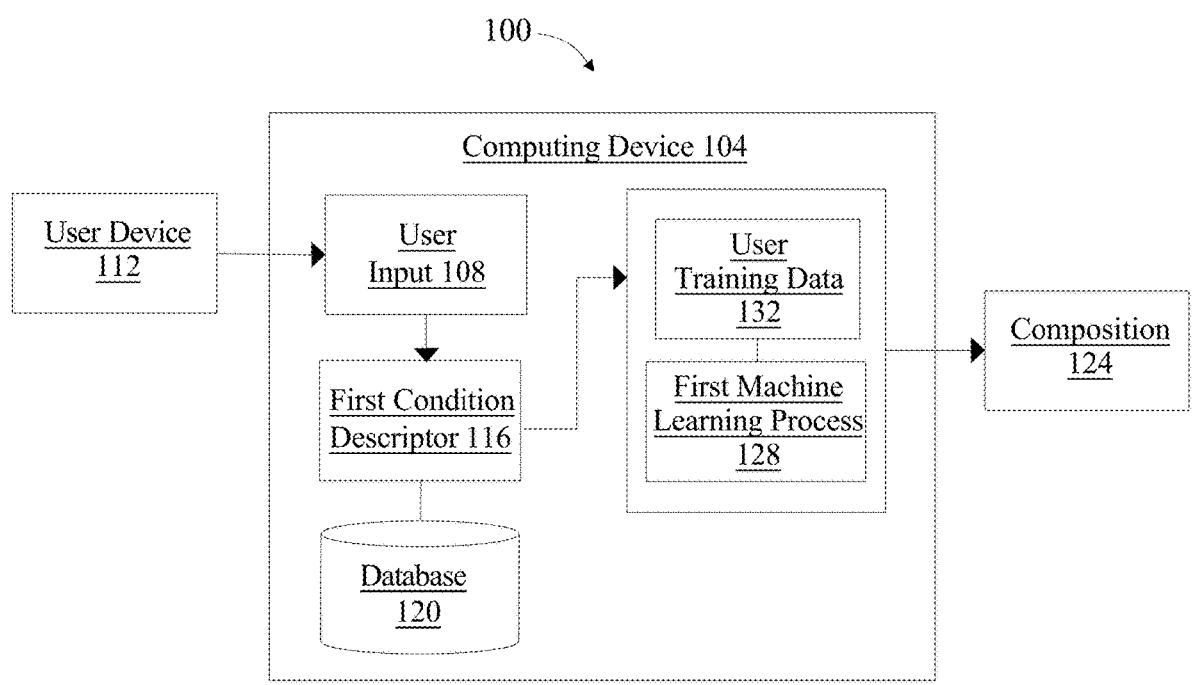
FIG. 1 is a block diagram of an exemplary embodiment of an apparatus for determining a composition of a replacement therapy treatment.

Now referring to FIG. 1, an exemplary embodiment of a block diagram of an apparatus for determining a composition of a replacement therapy treatment is illustrated. Apparatus 100 comprises at least a processor and a memory communicatively connected to the processor, the memory containing instructions configuring the at least a processor to perform steps as described herein. At least a processor may be a computing device 104. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, Computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 is configured to receive a user input 108. User input 108 may be received from a user device 112. In this disclosure, a "user input" is a piece of data received from a user, possibility through a remote user device. "User device" may include without limitation, a display in communication with computing device 104, where a display may include any display as described herein. User device may include an additional computing device, such as a mobile device, laptop, desktop, computer, and the like. In an embodiment, user device may have a touch screen to interact with the user. User may input user input 108 through user device. Any of user inputs 108 may be input via user inputs 108 at user device 112, and/or retrieved from database 120. Additionally, user device 112 may use a remote sensor to obtain user input 108. A "remote sensor," as used in this disclosure, is a device that captures data of human subject and transmits that data to computing device 104, either by transmitting the data to user device which relays the data to computing device 104, or by transmitting the data separately over a network connection. User input 108 may be transmitted via communication channel interface and/or via a separate network connection formed, for instance, using a secure sockets layer (SSL) and/or hypertext transfer protocol-secure (HTTPS) process. User inputs 108 may include any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. User input 108 may include, but not limited to any medical test, a user's health assessment, a user's constitutional history, an assessment conducted in any website providing information related to a medical condition, a direct entry from a user, and the like. As a non-limiting example, and without limitation, user input 108 describing red blood cells may be recognized as useful for identifying various conditions such as dehydration, high testosterone, nutrient deficiencies, kidney dysfunction, chronic inflammation, anemia, and/or blood loss. For instance, and without limitation, a particular set of biomarkers, test results, and/or biochemical information may be recognized in each medical field as useful for identifying various disease conditions or prognoses within a relevant field.

Continuing to refer to FIG. 1, user input 108 comprises at least an identifier. The input may include an identifier. An "identifier" as used in this specification is a unique, non-changing alphanumeric set of characters of any length for each user. Identifier may link a user to a medical record, or an electronic health record associated with the user. The identifier may include a specific sequence of characters, numbers, letters, and/or words that may identify a user. The identifier may include a globally recognized uniform identifier such as a uniform code commission (UCC) barcode. The identifier may be directly entered into computing device 104. For example, a barcode reader or an electronic pen may be used to enter the identifier directly into computing device 104. The identifier may accompany a request for laboratory services and/or request for a procedure. Moreover, in a non-limiting embodiment, identifier may include text strings describing user information. For example and without limitation, identifier may include name, contact information, constitutional history, illnesses, appointment history, test results etc. Person of ordinary skill in the art, upon reviewing the entirety of this disclosure, will be aware of highlighting terms and/or the various types of information and/or qualifications associated with a user that are relevant to generating first condition descriptor and the like thereof.

Continuing to refer to FIG. 1, user input 108 comprises a constitutional history of the user. As defined in this disclosure, the "constitutional history" of the user is defined as the user's medical past and present which may contain relevant information bearing on the user's medical past, present, and future. The constitutional history of the user may include, but not limited to the chief concern; the history of present illness, past constitutional history which may include pre-existing illnesses, medication history, and allergies; the family history which may include the family constitutional history as well as family behavioral history; the user's social history, questions related to the user's organs which may help establish the causes of signs and symptoms, and the like. The constitutional history of the user may be problem-focused, expanded problem-focused, comprehensive, and the like.

User input 108 may include a plurality of capillary density measurements. As defined in this disclosure, "capillary density" refers to the length of red cell-perfused capillaries per observation area (cm-1). Capillary density may include one or more measurements of glycocalyx thickness, one or more measurements of perfused boundary region, and/or a microvascular health score. For instance and without limitation, capillary density may include a Microvascular Health Score (MVHS) as produced by Glycocheck of Maastricht, Netherlands. For instance, capillary density refers to the number of capillaries present at a certain site in the human body. Measuring capillary density may provide information that may help diagnose a user with a potential disease. For instance, loss of capillary density, and thus flow of blood through tissues, may be considered a feature of aging. Such loss of blood flow may provide an indication that a user may be at risk for, for example, heart disease. In another non-limiting example, loss of capillary density may be associated with connective tissue diseases ("CTD"). "CTD," as used in this disclosure, are a diverse group of rheumatologic disorders characterized by the presence of autoantibodies and systemic organ involvement, frequently including the lung or chest. An experimental setup may include, but not limited to a sidestream dark field ("SDF") camera (CapiScope HVCS, KK Technology, Honiton, UK). was used to visualize the sublingual microvasculature. The dynamic lateral movement of red blood cells ("RBCs") is measured which provides an indication as to the capillary density. The plurality of capillary density measurements are measured using sublingual video microscopy. In this case, the camera, such as the SDF camera, is positioned towards the sublingual mucosa and maneuvered until a clear image of the microcirculation is acquired. As an example, the camera may use green light emitting stroboscopic diodes (540 nm) to detect the hemoglobin of passing red blood cells (RBCs). With the use of, for example, a 5× objective with a 0.2 numerical aperture, images are captured, providing a 325-fold magnification in 720×576 pixels at 23 frames per second. Each complete measurement may consist of, at least ten 2-second videos (40 frames/video), containing a total of about 3000 vascular segments of 10 μm length each. All videos are deliberately obtained from different positions to counterbalance spatial heterogeneity of the sublingual microcirculation.

Additionally or alternatively, with continued reference to FIG. 1, user input 108 may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. User input 108 may include, without limitation, immune function data such as Interleukine-6 (IL-6), TNF-alpha, systemic inflammatory cytokines, and the like.

Continuing to refer to FIG. 1, user input 108 may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. User input 108 may include measures of glucose metabolism such as fasting glucose levels and/or hemoglobin A1-C (HbA1c) levels. User input may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. User input 108 may include measures of estimated glomerular filtration rate (eGFR). User input 108 may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. User input 108 may include peptides, lipid analysis, growth factors, micro-RNA, RNA, and genetic data. User input 108 may include one or more markers including but not limited to antinuclear antibody levels, Rheumatoid factor, Sjogren's antibodies, Anti-Tubulin, Associated with alcoholic liver disease, demyelinating disease, Grave's disease, Hashimoto's thyroiditis, infectious agent exposure PANDAS/ANDAS/OCD, rheumatoid arthritis, and recent onset type 1 diabetes, Anti-Myelin basic protein, Related to the risk for multiple sclerosis, autism, PANDAS/ANDAS/OCD, and systemic lupus erythematosus (SLE), an autoimmune condition, COVID-19, Anti-Myelin oligodendrocyte glycoprotein (MOG), Found in various demyelinating diseases, including multiple sclerosis, neuromyelitis optica spectrum disorders (NMOSD), idiopathic optic neuritis (ON), acute disseminated encephalomyelitis (ADEM), multiphasic disseminated encephalomyelitis (MDEM), Devic's disease, and tumefactive demyelinating disease, Anti-Myelin proteolipid protein, A useful marker in patients with seronegative anti-myelin basic protein, the frequent marker in active multiple sclerosis and optic neuritis, Anti-Neurofascin, Found mainly in combined central and peripheral demyelination (CCPD), a rare demyelinating condition affecting both CNS and peripheral nervous system (PNS) tissues, and also in chronic inflammatory demyelinating polyneuropathy (CIDP) and axonal injury in patients with multiple sclerosis (MS), Anti-MAG, Anti-MAG peripheral neuropathy is a very rare disease caused by anti-MAG antibodies that destroy MAG protein leading to disruptions of normal myelin production and healthy peripheral nerve activity.

With continued reference to FIG. 1, user input 108 may include one or more markers of blood brain barrier disruption, including but not limited to Anti-s100b, Blood brain barrier integrity breach and sub-concussive episodes lead to the production of this antibody. Extravasated s100B may trigger a pathologic autoimmune reaction linking systemic and CNS immune responses, Anti-Glial fibrillary acidic protein, Anti-GFAP is produced when the protein enters the bloodstream after a rupture of the blood brain barrier, thus serves as a blood based diagnostic marker of brain injury, Anti-Microglia, Indicate a destruction of the blood brain barrier and are found to play a role in tissue destruction of Alzheimer's disease, Anti-Glucose regulated protein 78, Glucose-regulated protein 78-targeted antibodies could instigate blood brain barrier breakdown and development of hallmark anti-aquaporin-4 autoantibody pathology.

With continued reference to FIG. 1, user input 108 may include one or more markers of optical and/or autonomic nervous system disorders including but not limited to Anti-Neuron specific enolase, Antibodies against neuron specific enolase are found in patients with optical neuropathies, Anti-Aquaporin 4, AQP4 IgG is involved in the development of neuromyelitis optica and revolutionized the understanding of the disease. Anti-Aquaporin4 antibodies have also been shown in patients with peripheral demyelination, Anti-Recoverin, One of the key components of antibody disorders of the CNS. They have also been shown to be associated with retinopathy which is characterized by impaired vision and photosensitivity, Anti-CV2, Seen in autoimmune paraneoplastic autonomic neuropathy and mixed axonal and demyelinating peripheral neuropathy and the like.

With continued reference to FIG. 1, user input 108 may include one or more markers of peripheral neuropathy, including but not limited to Anti-GM1, Associated with multi-focal motor neuropathy and lower motor neuropathy, characterized by muscle weakness and atrophy, Anti-GM2, A potential peripheral nerve antigen for neuropathy-associated autoantibodies, Anti-Hu, The most frequent manifestation of sensory neuropathy with frequent autonomic involvement, Anti-Ri, Can be detected in patients with the paraneoplastic opsoclonus/myoclonus syndrome. Neoplasms most often associated with anti-Ri include breast cancer, gynecological cancers, and small cell lung cancer, Anti-Amphiphysin, Often found in the serum of patients with stiff-person syndrome and the like.

With continued reference to FIG. 1, user input 108 may include one or more markers of neuromuscular disorders, including but not limited to Anti-Acetylcholine receptors, Found in myasthenia gravis disease which destroys the receptor function, leading to a neuromuscular transmission defect, which then causes hypofunction, fatigue, and inflammation of skeletal muscles and produces serum antibodies against muscle antigens, Anti-Muscle specific kinase, An important marker in patients without anti-acetylcholine receptor antibodies in myasthenia gravis disease, Anti-Voltage gated calcium channels, Responsible for Lambert-Eaton myasthenic syndrome (LEMS), a rare autoimmune disorder of the neuromuscular junction, Anti-Voltage gated potassium channels, Downregulate the potassium channels expressed on the peripheral nerve terminal leading to nerve hyperexcitability, Anti-Titin, Present in 70-90% of thymoma autoimmune myasthenia gravis (MG) patients, and in approximately 50% of late-onset acetylcholine-MG patients without thymoma and the like.

With continued reference to FIG. 1, user input 108 may include one or more markers of brain autoimmunity, including but not limited to Anti-Purkinje cell, Autoimmunity to a class of GABAergic neurons located in the cerebellum, which can produce abnormalities and decline in gross motor functions, Anti-Yo, Suggest that a patient with neurologic symptoms has a paraneoplastic syndrome. In addition, their presence also often suggests the nature of the underlying tumor, Anti-Amyloid beta (25-35), Levels of autoantibodies reacting with oligomers of the short, neurotoxic fragment Aβ (25-35) are significantly higher in AD patients than in healthy controls, Anti-Amyloid beta (1-42), A signature marker in Alzheimer's disease, Anti-RAGE peptide, Found in Alzheimer's disease patients, and particularly higher in AD patients with diabetes, Anti-Tau, Found in the neurofibrillary tangles in brains of individuals who have Alzheimer's disease, Anti-Glutamate, Found in epilepsy, encephalitis, cerebellar ataxia, systemic lupus erythematosus (SLE) and neuropsychiatric SLE, Sjogren's syndrome, schizophrenia, mania or stroke, Anti-Dopamine, Associated with movement disorders characterized by parkinsonism, dystonia, and Sydenham chorea, Anti-Hydroxytryptamine, Found mainly in autoimmune encephalitis, Anti-Alpha-synuclein, Mainly elevated in Parkinson's disease and Alzheimer's disease, Anti-α1 and β2 adrenergic receptors, Found mainly in patients with different dementia forms such as unclassified, Lewy body, vascular, and Alzheimer's dementia, Anti-Endothelin A receptor, Found in vascular dementia and the like.

With continued reference to FIG. 1, user input 108 may include one or more markers of brain inflammation, including but not limited to Anti-NMDA receptor, Found in anti-NMDA receptor encephalitis, Anti-AMPA receptor, May play a role in Alzheimer's disease, characterized by decreased AMPA activation and synapse loss, Anti-Dopamine receptors, Associated with Parkinson's disease and other disorders of low dopamine status, Anti-GABA receptors, Associated with temporal lobe epilepsy (TLE), Parkinson's disease (PD) and Huntington's disease (HD) and other neurodegenerative disorders that involve disruptions in gamma-amino butyric acid (GABA) signaling, Anti-Dipeptidyl aminopeptidase-like protein 6, Associated with encephalitis, Anti-Glycine receptor, Helpful in the diagnosis of patients with symptoms and signs that include ocular motor and other brainstem dysfunction, hyperekplexia, stiffness, rigidity, myoclonus and spasms, Anti-Neurexin 3, Associated with a severe but potentially treatable encephalitis in which the antibodies cause a decrease of neurexin-3a and alter synapse development, Anti-Contactin-associated protein-like 2, Diseases associated with CNTNAP2 include Pitt-Hopkins-Like Syndrome 1 and Autism 15, Anti-Leucine-rich glioma-inactivated protein 1, LGI1 antibody-associated encephalitis has increasingly been recognized as a primary autoimmune disorder, Anti-Ma, Present in men with testicular tumors and isolated or combined limbic encephalitis (LE), diencephalic encephalitis (DE), or brainstem encephalitis (BE) and the like.

With continued reference to FIG. 1, user input 108 may include one or more markers of infection, including but not limited to Anti-HSV-1, HSV-1 has been reported to have a pathogenesis role in Herpes simplex encephalitis (HSE) and seropositivity to HSV-1 antibodies has been correlated with increased risk of Alzheimer's disease, Anti-HSV-2, Herpes simplex encephalitis (HSE) is a disorder commonly associated with HSV-2. HSE due to HSV-2 may occur without meningitis features. Antibodies against HSV-2 have shown positive correlation in patients with symptoms of HSE, Anti-EBV, Antibodies against the EBV nuclear antigen complex (EBNAc) and EBNA-1 have been correlated with increased risk of multiple sclerosis (MS), Anti-CMV, Cytomegalovirus (CMV) infections have been reported frequently to be associated with Guillain-Barre syndrome (GBS). There is a potential for molecular mimicry between GM2 and antigens induced by CMV infection, Anti-HHV-6, Human herpesvirus-6 (HHV-6) is frequently associated with neurologic diseases, including multiple sclerosis (MS), epilepsy, encephalitis, and febrile illness, Anti-HHV-7, HHV-7 has been less frequently associated with CNS disease than HHV-6, but found to be associated with encephalitis, meningitis, and demyelinating conditions. Similar to HHV 6A, increased levels of HHV-7 were found in multiple brain regions in Alzheimer's disease (AD) patients, Anti-Streptococcal A, Anti-streptococcal A antibodies are shown to cross react with different brain proteins that could lead to neuropsychiatric symptoms including PANDAS characterized by pediatric obsessive-compulsive disorder and the like.

With continued reference to FIG. 1, user input 108 may include one or markers including but not limited to aluminum, mercury, lead, cadmium, or arsenic levels. User input 108 may include arsenic levels. User input 108 may include levels of fibrinogen, plasma cystatin C, and/or brain natriuretic peptide, Neuron specific enolase (NSE), Glial fibrillary acidic protein (GFAP), Amyloid beta, Abeta 1-42, Abeta 1-40, Abeta42/Abeta40 ratio, Total Tau, s100b, Neurofilament light, alpha synuclein, Brain-derived neurotrophic factor (BNDF) and the like. In an embodiment, user input 108 may be obtained from one or more measurements of blood and/or cerebrospinal fluid (CSF).

Continuing to refer to FIG. 1, user input 108 may include measures of lung function such as forced expiratory volume, one second (FEV-1) which measures how much air can be exhaled in one second following a deep inhalation, forced vital capacity (FVC), which measures the volume of air that may be contained in the lungs. User input may include a measurement blood pressure, including without limitation systolic and diastolic blood pressure. User input may include a measure of waist circumference. User input 108 may include body mass index (BMI) or measurements of Intracellular and Extracellular Water, Phase Angle, Body composition, lean body mass, fat mass, All measured via Bioimpedance Analysis. User input may include one or more measures of bone mass and/or density such as dual-energy x-ray absorptiometry. User input 108 may include one or more measures of muscle mass. User input 108 may include one or more measures of physical capability such as without limitation measures of grip strength, evaluations of standing balance, evaluations of gait speed, pegboard tests, timed up and go tests, and/or chair rising tests.

With continued reference to FIG. 1, user input 108 may include, without limitation any result of any medical test and/or physiological assessments, or the like. A medical test may include but is not limited to a positron emission tomography (PET) scan, a computed tomography scan (CT), a magnetic resonance imaging (MRI), ultrasound, an electroencephalogram (EEG), a quantitative EEG, any neuropsychological testing and the like. For instance, user input may include any medical tests and/or results used to diagnose a renal disorder, such as a glomerular filtration rate test ("GFR"). "GFR," as used in this disclosure, is a urine test to check for albumin. Albumin is a protein that can pass into the urine when the kidneys are damaged. In an embodiment, user input 108 may include any marker of autoantibodies, toxicity, inflammation, cellular senescence, autophagy, mitochondrial function, neurodegeneration and the like.

Still referring to FIG. 1, user input 108 may include other cardiovascular data such as heart rate data, blood pressure data, or the like, for instance captured using audio and/or oximetry devices. User input may include respiratory data such as audio capture of pulmonary sounds using a microphone or the like. User input 108 may include neurological data. User input 108 may include digestive audio data. User input 108 may include visual data captured regarding one or more elements of externally visible patient anatomy. User input 108 may capture one or more elements of human subject bodily motion, including gait, posture or gestural motions. In an embodiment, User input 108 may include glycocalyx-related biomarkers, as explained above.

Additionally, user device may use a remote sensor to obtain user input 108. A "remote sensor," as used in this disclosure, is a device that captures data of human subject and transmits that data to computing device 104, either by transmitting the data to user input device which relays the data to computing device 104, or by transmitting the data separately over a network connection. User input 108 may be transmitted via communication channel interface and/or via a separate network connection formed, for instance, using a secure sockets layer (SSL) and/or hypertext transfer protocol-secure (HTTPS) process. Remote sensor may include, without limitation, a camera such as a digital camera incorporated in a mobile device or the like, a microphone such as a mobile device microphone, a motion sensor, which may include one or more accelerometers, gyroscopes, magnetometer, or the like. Remote sensor may include one or more peripheral devices such as a peripheral pulse oximeter or the like. Remote sensor may include a network-connected device such as a network connected digital scale or the like. In an embodiment, remote sensor may be used to capture audio or visual data concerning one or more portions of human subject's anatomy. For instance, and without limitation, a microphone may be pressed against one or more portions of human subject at direction of user over communication channel, causing capture of audio data from the one or more portion of human subject; as a non-limiting example, audio data of human subject lungs, heart, digestive system, or the like may be so captured. As a further example, user may instruct human subject to train a camera on one or more portions of anatomy to capture visual data concerning such one or more portions. Such physiological data may be combined; for instance, audio capture of circulatory system noise data may be combined with pulse oximetry data from a peripheral pulse oximeter and/or motion-sensor data indicating a degree of activity. Remote sensor may include an electrical sensor such as a portable electrocardiogram device or the like. Generally, any sensor capable of capturing data of human subject and transmitting such data locally or over a network may be used as a remote sensor.

Still referring to FIG. 1, computing device 104 is also configured to generate a first condition descriptor 116 as a function of user input 108. Computing device 104 may generate first condition descriptor 116 as a function of user input 108 or may be received within user input 108. As defined in this disclosure, "first condition descriptor" is data describing a first condition; a "first condition" is a disease, illness, or injury that may be treated or in need of treatment by a medical professional of a replacement therapy treatment. A first condition descriptor 116 may include any physiologic, mental, or psychological condition or disorder. Non-limiting examples of first condition descriptor 116 may include atherosclerosis, cardiovascular disease, adult cancer, arthritis, cataracts, osteoporosis, type 2 diabetes, hypertension, neurodegeneration (including but not limited to Alzheimer's disease, Huntington's disease, and other age-progressive dementias; Parkinson's disease; and amyotrophic lateral sclerosis [ALS]), stroke, atrophic gastritis, osteoarthritis, NASH, camptocormia, chronic obstructive pulmonary disease, coronary artery disease, dopamine dysregulation syndrome, metabolic syndrome, effort incontinence, Hashimoto's thyroiditis, heart failure, late life depression, immunosenescence (including but not limited to age related decline in immune response to vaccines, age related decline in response to immunotherapy etc.), myocardial infarction, acute coronary syndrome, sarcopenia, sarcopenic obesity, senile osteoporosis, urinary incontinence etc. A first condition descriptor may be related to a change in blood parameters, heart rate, cognitive functions/decline, bone density, basal metabolic rate, systolic blood pressure, heel bone mineral density (BMD), heel quantitative ultrasound index (QUI), heel broadband ultrasound attenuation, heel broadband ultrasound attenuation, forced expiratory volume in 1-second (FEV1), forced vital capacity (FVC), peak expiratory flow (PEF), duration to first press of snap-button in each round, reaction time, mean time to correctly identify matches, hand grip strength (right and/or left), whole body fat-free mass, leg fat-free mass (right and/or left), and time for recovery after any stress (wound, operation, chemotherapy, disease, change in lifestyle etc.). Embodiments of the first condition descriptor may include a cardiovascular disease, bone loss disorder, a neuromuscular disorder, a neurodegenerative disorder or a cognitive disorder, a metabolic disorder, sarcopenia, osteoarthritis, chronic fatigue syndrome, senile dementia, mild cognitive impairment, schizophrenia, Huntington's disease, Pick's disease, Creutzfeldt-Jakob disease, stroke, CNS cerebral senility, age-related cognitive decline, pre diabetes, diabetes, obesity, osteoporosis, coronary artery disease, cerebrovascular disease, heart attack, stroke, peripheral arterial disease, aortic valve disease, stroke, Lewy body disease, amyotrophic lateral sclerosis (ALS), mild cognitive impairment, pre-dementia, dementia, progressive subcortical gliosis, progressive supranuclear palsy, thalamic degeneration syndrome, hereditary aphasia, myoclonus epilepsy, macular degeneration, or cataracts, hair loss, hair greying, and the like. Additionally, first condition descriptor 116 may be caused by a pathogen such as bacteria, archaea, protists, fungi, infections proteins such as prions, parasitic multicellular organisms such as nematodes including without limitation ascarids and/or filarial worms, flatworms including without limitation flukes and tapeworms, insectoid parasites such as without limitation botflies and/or screw worms, or the like. In an embodiment, first condition descriptor 116 may be caused by a corona virus. In this disclosure, a "corona virus" refers to a large family of viruses that cause illness ranging from the common cold to more severe diseases.

Still referring to FIG. 1, computing device 104 may connect to and/or include a database 120. Database 120 may be implemented, without limitation, as a relational database 120, a key-value retrieval database 120 such as a NOSQL database 120, or any other format or structure for use as a database 120 that a person skilled in the art would recognize as suitable upon review of the entirety of this disclosure. Database 120 may alternatively or additionally be implemented using a distributed data storage protocol and/or data structure, such as a distributed hash table or the like. Database 120 may include a plurality of data entries and/or records as described above. Data entries in a database 120 may be flagged with or linked to one or more additional elements of information, which may be reflected in data entry cells and/or in linked tables such as tables related by one or more indices in a relational database 120. Persons skilled in the art, upon reviewing the entirety of this disclosure, will be aware of various ways in which data entries in a database 120 may store, retrieve, organize, and/or reflect data and/or records as used herein, as well as categories and/or populations of data consistently with this disclosure. In some embodiments, network data, or other information such as user information, transfer party information, and alimentary provider information, may be stored in and/or retrieved from database 120. Database 120 is further described herein with reference to FIG. 2.

Referring still to FIG. 1, generating first condition descriptor 116 may further comprise identifying a plurality of biomarkers as a function of user input 108. A "biomarker", as used in this disclosure, is a biological and/or chemical substance or process that is indicative of a particular functioning in the body. Plurality of biomarkers may include, without limitation, red blood cell count, hemoglobin levels, hematocrit, mean corpuscular volume, mean corpuscular hemoglobin, and/or mean corpuscular hemoglobin concentration. The presence of at least one biomarker may indicate a likelihood that a user is currently experiencing or might experience some disease at a future date. For instance, early detection of tumor necrosis factor-alpha (TNF) from the TNF cytokine family which triggers many intracellular processes may indicate that the user may be experiencing or will experience symptoms of, rheumatoid arthritis, for example. Plurality of biomarkers may include, for example, monitoring biomarkers. A "monitoring biomarker," as used in this specification, is a biomarker that may be used to assess the progress of a disease or to monitor the effects of a therapeutic agent, such as, for example, administration of a course of antibiotics. In another example, a biomarker may be a diagnostic biomarker. A "diagnostic biomarker," as defined in this disclosure is a biomarker that is used to detect the presence of a disease or a condition of interest. Another example of a biomarker is a predictive biomarker. A "predictive biomarker," as used in this disclosure, is a biomarker used to predict what group of patients will respond favorably or unfavorably to a particular treatment. In an embodiment, plurality of biomarkers may include a predictive biomarker. Examples of plurality of biomarkers that may be used in diagnosing a, for instance, type-2 diabetes may include branched chain amino acids (BCAA) which may be associated with hyperglycemia and may be a predictive biomarker for type-2 diabetes. Other potential predictive biomarkers of diabetes risk include dimethylglycine (DMG), 2-amino adipic acid, and glycine.

Plurality of biomarkers may be extracted, for example, chemically. For instance, an enzyme-linked immunosorbent assay ("ELISA") may be used to identify at least one disease biomarker. For instance, the presence of Interleukin IL-1β (IL-1β) and/or matrix metalloproteinase (MMP-9) may indicate the potential for the presence of a renal disease. Plurality of biomarkers may be extracted, for example, from a research journal. Alternatively, plurality of biomarkers may be extracted by experimentation. For example, a biomarker that may indicate a particular disease may incorporate testing for the presence of a biomarker using a control group where the group does not have the biomarker present. Values for the biomarker for a sample group known to have the biomarker present may be compared against the values obtained for the control group and a determination made regarding the presence of a particular disease.

Still referring to FIG. 1, generating first condition descriptor 116 may further comprise calculating a value for each biomarker of the plurality of biomarkers in a biological sample. As used in this disclosure, a "value" is a numerical measure of presence of a particular biomarker. In an embodiment, the plurality of biomarkers may be determined by statistical methods. A kidney disorder, for example, may be indicated by changes in a value for each biomarker within a particular range of neutrophil gelatinase-associated lipocalin (NGAL). A value for each biomarker within a suitable range for a marker may, for example, indicate the absence of a particular health condition. A value outside the suitable range may indicate, for example, the presence of a particular health condition. A value for each biomarker considered outside the suitable range may indicate a value that is higher or lower than a value included within the suitable range. A value for each biomarker may be a value published in, for example, a research journal. Alternatively, a value for each biomarker may be determined by experimentation. For example, an analysis of a renal disorder may include a control experiment to determine the values of a particular value for each biomarker that fall within the suitable range. After the control experiment, a urine sample, for instance, may be analyzed and a measurement for a value for a particular biomarker made and compared to the value of the control sample. A patient may be suffering from a renal disorder if, for example, the value of a value for a particular biomarker falls outside the suitable range of values of the value for the control experiment. A value for the value for a biomarker that is higher or lower than the suitable range may result in a positive result for a renal disorder.

For example, data reduction methods may be used to obtain the type of biomarkers. Data reduction statistical methods may include, but not limited to trend analysis, clustering, and the like. Classification algorithms may also be utilized to determine the plurality of biomarkers. Such statistical methods include, but not limited to, regression, support vector machine, decision trees and random forests, artificial neural networks, and gene relationship analysis. Another category of statistical methods may include visualization. Statistical methods in this category may include, but not limited to, Principal Component Analysis, Network analysis, and the like. Values for biomarkers may be determined from a biological sample. A "biological sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Biomarkers may be determined from the physical sample and transmitted to computing device 104.

Referring still to FIG. 1, computing device 104 is further configured to determine a composition 124 of a replacement therapy treatment as a function of first condition descriptor 116. As used herein, a "replacement therapy treatment" is an process for remediation of a therapeutic health problem and/or imbalance, where the process for remediation includes replacement of plasma in the user's bloodstream. Replacement therapy treatment may include plasma exchange treatment. As used in this specification, a "plasma exchange treatment" is defined as the removing plasma from the body and the replacing the plasma with plasma replacement therapy treatment. "Plasma," as used in this disclosure, is the liquid portion of blood. Health conditions suitable for plasma exchange treatment may include, without limitation, treatment of neurological conditions such as Guillain-Barre Syndrome, chronic inflammatory demyelinating polyneuropathy, Alzheimer's disease, Parkins's disease, unspecified neurodegenerative conditions and the like. Non-neurologic conditions such as Myasthenia Gravis, hyperviscosity syndrome, thrombotic thrombocytopenic purpura, haemolytic uremic syndrome, idiopathic thrombocytopenia, long COVID, PASC and the like, may be suitable for plasma exchange treatment. Other conditions may include, but not limited to, transplant rejection of solid organs such as the kidneys and heart, multiple sclerosis, and the like. Additionally, replacement therapy treatment may include a composition of plasma protein concentrate that is used to replace human plasma in the bloodstream of the user, as explained below. In an embodiment, plasma exchange treatment and replacement therapy may be utilized to improve cellular habitat so as to modify tissued based and/or exogenous stem cells behavior to effect multi-tissue regeneration. Replacement therapy treatment may include a series of one or more ingredients given to a user at the same time and/or in a sequence of treatments given our a specified period of time. For example, replacement therapy may include a single infusion containing two ingredients given to a user in the course of one treatment. In yet another non-limiting example, a replacement therapy may include a series of infusions containing a multiple of ingredients, with each ingredient given in a particular series of steps and at a particular period of time within the treatment. In an embodiment, replacement therapy treatment may be delivered to a user with any delivery mechanism including but not limited to oral delivery, intravenous delivery, subcutaneous delivery, intranasal delivery, rectal delivery, vaginal delivery, dermal delivery and the like. In an embodiment, replacement therapy treatment may include one or more additional therapies given before, during, and/or after delivery of replacement therapy treatment. An "additional therapy," as used in this disclosure, is any therapy given in addition to replacement therapy treatment. An additional therapy may include but is not limited to a prescription medication, supplement, food, exercise program, over the counter medication, a homeopathic remedy, a natural medicine, an herbal extract and the like. For example, a user may be prescribed an oral supplement such as bromelain 400 mg to be taken twice daily for 3 days prior to receiving a replacement therapy treatment.

In this disclosure, a "composition" refers to the makeup and ingredients used to create the replacement therapy treatment. Composition 124 of the replacement therapy treatment may comprise albumin. Albumin may be present in an amount ranging from at least about 30 grams per liter to about 60 grams per liter. Additionally, composition 124 may comprise a plasma protein concentrate. Composition 124 of the replacement therapy treatment may comprise a solution of electrolytes. Composition 124 may include one or more immunoglobulins, trace mineral, complex biological molecules such as extracts or derivations of plant material, biosimilar molecules, molecules intended for the purpose of chelation of cationic toxins, and the like. Composition 124 of the replacement therapy treatment may comprise lipids. Composition 124 of the replacement therapy treatment may comprise proteins and peptides. Composition 124 of the replacement therapy treatment may comprise immunoglobin concentrates. Composition 124 of the replacement therapy treatment may comprise stem cells and products of stem cells such as exosomes. Composition 124 of the replacement therapy treatment may comprise vitamins. Composition 124 of the replacement therapy treatment may comprise ions. Furthermore, generating first condition descriptor 116 further comprises identifying a plurality of biomarkers as a function of the user input 108, calculating a value for each biomarker of the plurality of biomarkers in a biological sample, training a second machine-learning process using a reference biomarker training data wherein the reference biomarker training data correlates reference values for each biomarker to first conditions 116, and determining first condition descriptor 116 as a function of the value for each biomarker of the plurality of biomarkers and the second machine learning process.

Determining composition 124 may include training a first machine-learning process 128 using user training data 132. As used herein, "training data," as used herein, is data containing correlations that a machine-learning process may use to model relationships between two or more categories of data elements. User training data 132 may be received and/or collected from experts or from users that may have may have been diagnosed with a health condition with particular disease markers where exchange treatment improved and/or cure the health condition. User training data 132 may be received as a function of determinations of a health condition based on disease markers, health condition metrics, and/or measurable values. User training data 132 set may be received and/or otherwise developed during one or more past iterations of the previous user training data vectors. User training data 132 may be received from one or more remote devices that at least correlate a biomarker and its correlating value to a composition 124, where a remote device is an external device to computing device 104. or instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in user training data 132 according to various correlations; correlations may indicate causative and/or predictive links between categories of data elements, which may be modeled as relationships such as mathematical relationships by machine learning processes as described in further detail below. User training data 132 may be formatted and/or organized by categories of data elements, for instance by associating data elements with one or more descriptors corresponding to categories of data elements. As a non-limiting example, user training data 132 may include data entered in standardized forms by persons or processes, such that entry of a given data element in a given field in a form may be mapped to one or more descriptors of categories. Elements in user training data 132 may be linked to descriptors of categories by tags, tokens, or other data elements; for instance, and without limitation, user training data 132 may be provided in fixed-length formats, formats linking positions of data to categories such as comma-separated value (CSV) formats and/or self-describing formats such as extensible markup language (XML), enabling processes or devices to detect categories of data. User training data 132 correlates user inputs 108 to compositions 124 of the replacement therapy treatment. Composition 124 is then determined as a function of user input 108 and first machine learning process 128. The determination of the composition may further include determining the composition, where the first machine-learning process receives a first condition descriptor as an input and outputs the composition of the replacement therapy treatment. Computing device 104 outputs the composition of the replacement therapy treatment to the user device.

Referring still to FIG. 1, computing device 104 may be configured to train a second machine-learning process using a reference biomarker training data to generate first condition descriptor 116. Reference biomarker training data may correlate reference values for each biomarker to first conditions 116. First condition descriptor 116 may then be determined as a function of the value for each biomarker of the plurality of biomarkers and the second machine learning process. The reference biomarker training data may then correlate a reference value for each biomarker to a first condition. Computing device 104 may then determine first condition descriptor 116 where the second machine-learning model receives the value for biomarker as an input and outputs a first condition. The machine-learning process is described below in this disclosure with reference to FIG. 3. In an embodiment, computing device 104 may iteratively regenerate the reference biomarker training data as a function of first condition. The second machine-learning model is retrained using the regenerated biomarker training data. For example, new conditions that may involve new biomarkers may be incorporated into the training data and correct for model drift or predictive performance degradation.

Computing device 104 may then iteratively regenerate the reference biomarker training data as a function of the first condition descriptor and retrain the second machine-learning process using regenerated biomarker training data. As used in this disclosure, "iteratively regenerate" means repeatedly update the training data every time each first condition descriptor 116 is outputted. The second machine-learning model may be retrained using the regenerated biomarker training data. second machine-learning model may be trained, for example but without limitation, after each time the training data us updated, after a certain period of times, after the training data is updated a certain number of times, or the like. For example, new conditions that may involve new biomarkers may be incorporated into the training data and correct for model drift or predictive performance degradation.

Still referring to FIG. 1, computing device 104 is further configured to output composition 124 of the replacement therapy treatment as a function of the determination. For example, the composition may be outputted to a label that may be attached to an IV bag, a syringe, or the like. The composition may be outputted to the patient's Electronic Health Record where it can be retrieved and processed by a medical professional. The composition may be outputted to a location such as, but not limited to a compounding pharmacy or a laboratory equipped to prepare such compositions, where the composition may be outputted.

Referring back to FIG. 1, computing device 104 may be configured to determine the composition 124 of the replacement therapy treatment to treat a plurality of conditions. Plurality of conditions may occur at the same time. As used in this disclosure, a "plurality of conditions" are at least two health-related conditions that may affect the same or different systems in the human body where the patient is suffering from these conditions simultaneously. For example, one composition may be used in the replacement therapy treatment to treat a patient suffering from a cardiovascular ailment and a kidney issue. Another example may include a composition that may be used to treat a patient suffering from diabetic foot ulcers and diabetic neuropathy as a result of type-2 diabetes.

With continued reference to FIG. 1, system 100 further comprises a robot where the robot is designed and configured to prepare the composition of the replacement therapy treatment. As used herein, a "robot" refers to a programmable machine capable of carrying out a complex series of actions. Examples of robots include the ArXium (Buffalo Grove, Ill.) Riva™ system or the Grifols (Los Angeles, Calif.) KIRO® Fill Automated system or the Gri-fill Sterile Compounding Systgem and Gri-bag. Robot may include a plurality of components, such as servos. As used herein, "servos" refer to servo motors, which are rotary or linear actuators that rotate and push parts of a machine with precision. Another type of motor that the robot may also include is stepper motors. "Stepper motors" are DC motors that move in discrete steps by having multiple coils that are organized into groups; the rotor will rotate one step at a time. Robot may also be programmed through a communicative connection. As used in this disclosure, "communicatively connected" means connected by way of a connection, attachment or linkage between two or more relata which allows for reception and/or transmittance of information therebetween.

Furthermore, robot may also have a sensor. As used in this disclosure, a "sensor" is a device that is configured to detect a phenomenon and transmit information and/or datum related to the detection of the phenomenon. For instance, and without limitation, a sensor may transform an electrical and/or nonelectrical stimulation into an electrical signal that is suitable to be processed by an electrical circuit, such as a controller which is further explained below. A sensor may generate a sensor output signal, which transmits information and/or datum related to a detection by the sensor. A sensor output signal may include any signal form described in this disclosure, such as for example, digital, analog, optical, electrical, fluidic, and the like. In some cases, a sensor, a circuit, and/or a controller may perform one or more signal processing steps on a signal. For instance, a sensor, circuit, and/or controller may analyze, modify, and/or synthesize a signal in order to improve the signal, for instance by improving transmission, storage efficiency, or signal to noise ratio.

Robot may also possess an embedded processor or microcontroller separate from computing device 104. Microcontroller may include any sort of computing device. Microcontroller may include any computing device as described in this disclosure with reference to FIGS. 1 and 6, including without limitation a microcontroller, microprocessor, digital signal processor (DSP) and/or system on a chip (SoC) as described in this disclosure.

The robot may be configured to prepare a syringe that includes the composition of the replacement therapy treatment. The robot may be configured to prepare syringes with a volume of replacement therapy treatment ranging from about 1 ml to 60 ml. The robot may be configured to prepare an intravenous (IV) bag that includes the composition of the replacement therapy treatment. The robot may be configured to prepare an IV bag with a volume of replacement therapy treatment ranging from about 25 ml to 1,000 ml. The robot may be programmed to determine the exact dimensions of the IV bag. For example, the robot may be equipped with a barcode reader where the robot scans a barcode placed outside the bag, where the barcode contains the size of the bag. Once the size of the bag is determined, the movement by the robot may be optimized by using, for example, geometric programming or any other optimization algorithm. The robot may be configured to generate a label. For example, the label may contain, without limitation, a barcode containing the identifying information of a patient, the composition of the replacement therapy treatment, the date of compounding, an expiration date for the formulation, a signatory line, and the like.

Figure 2:
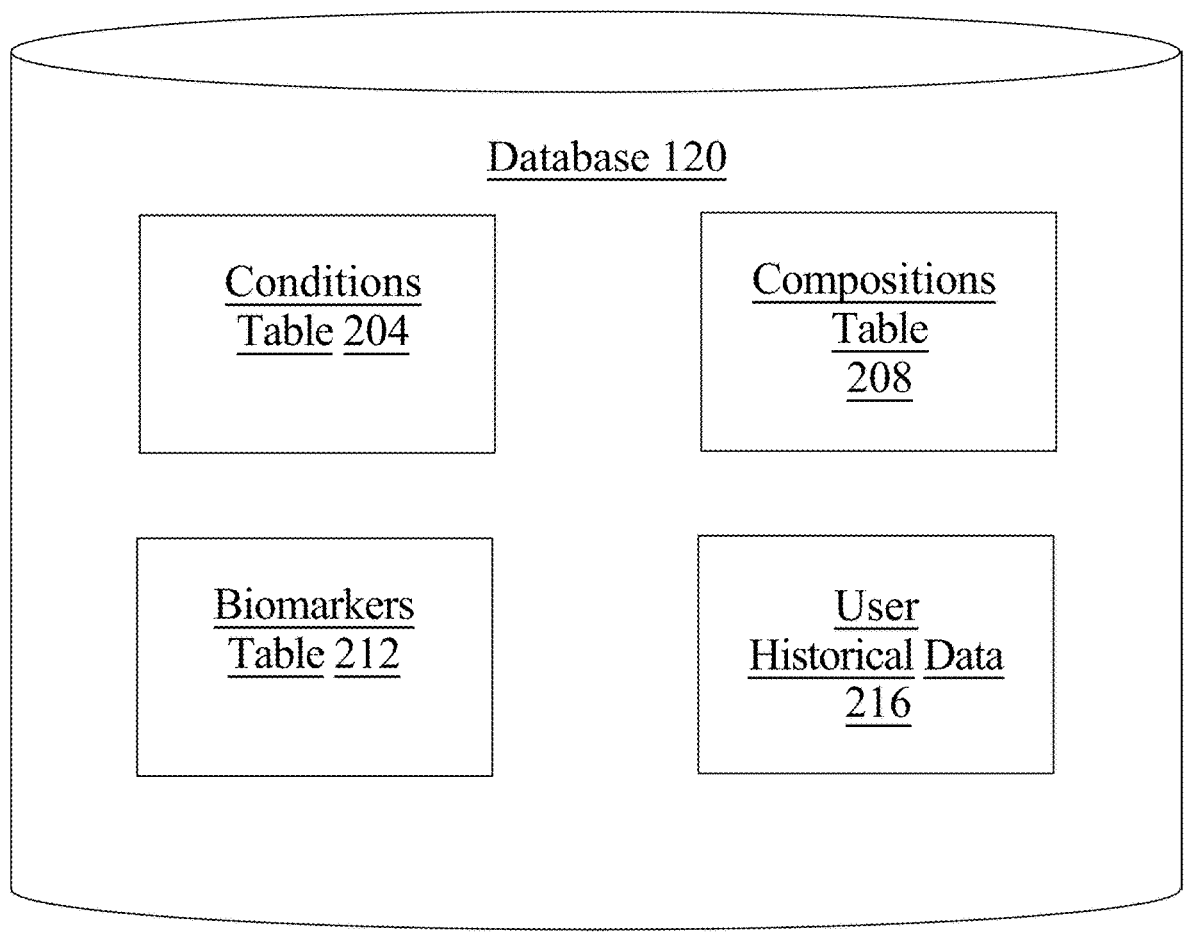
FIG. 2 is a block diagram of an exemplary embodiment of a database.

Now referring to FIG. 2, an exemplary embodiment of a database 120 is illustrated. Database 120 may, as a non-limiting example, organize data stored in the database according to one or more database tables. One or more database tables may be linked to one another by, for instance, common column values. "Common column values" are the sums of the values in all the expanded data cells in that column at the current row location. For instance, a common column between two tables of database 120 may include an identifier of a first condition, for instance as defined below; as a result, a query may be able to retrieve all rows from any table pertaining to a given first condition. Other columns may include any other category usable for organization or subdivision of data, including types of data, common pathways between, for example, an alimentary combination and a first alimentary provider, or the like; persons skilled in the art, upon reviewing the entirety of this disclosure, will be aware of various ways in which expert data from one or more tables may be linked and/or related to expert data in one or more other tables.

Still referring to FIG. 2, one or more database tables in database 120 may include, as a non-limiting example, a conditions table 204, which may be used to store records and attributes related to medical conditions. This may include, but not limited to, symptoms of the conditions, demographic of conditions, treatments, or the like. As another non-limiting example, one or more tables in database 120 may include a compositions table 208 which may be used to store regenerative treatment compositions 124 used to treat medical conditions, frequency of administration of treatment, and the like. As another non-limiting example, one or more tables in database 120 may include a biomarkers table 212. A biomarkers table 212 may include, but not limited to correlations of biomarkers to conditions, values of biomarkers reflecting the presence of a condition, data on biomarker research, and the like. As another non-limiting example, one or more tables in database 120 may include a user historical data table 216. A user historical data table 216 may include data from prior regenerative treatments administered to users, user outcome based on the treatment, frequency of treatment received for a particular user, and the like.

Figure 3:
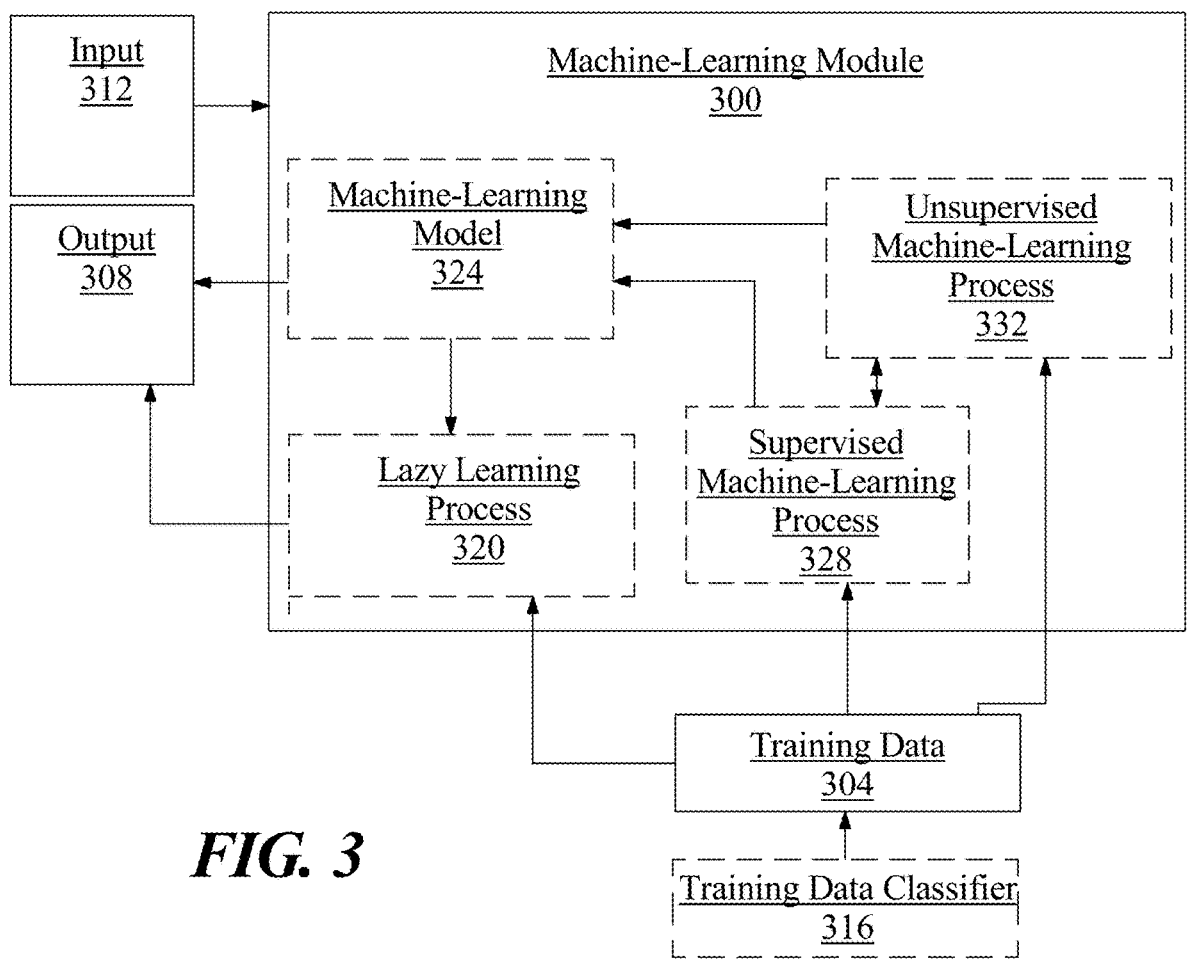
FIG. 3 is a block diagram of an exemplary embodiment of a machine-learning module.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example, biomarkers indicative of glycocalyx degradation may serve as inputs, outputting other potential health disorders that a may use the same disease biomarkers.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 300 may generate a classifier using a classification algorithm, defined as a process whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to classify biomarkers indicative of glycocalyx degradation into categories such as, for example, a target organ, and the like.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning model 324. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a disease biomarker such as TNF-α and a concentration outside a suitable range, renal disorder as an outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

With continued reference to FIG. 3, a "classifier," as used in this disclosure, is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a process whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 3, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)\div P(B)$, where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 3, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 3, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Figure 4:
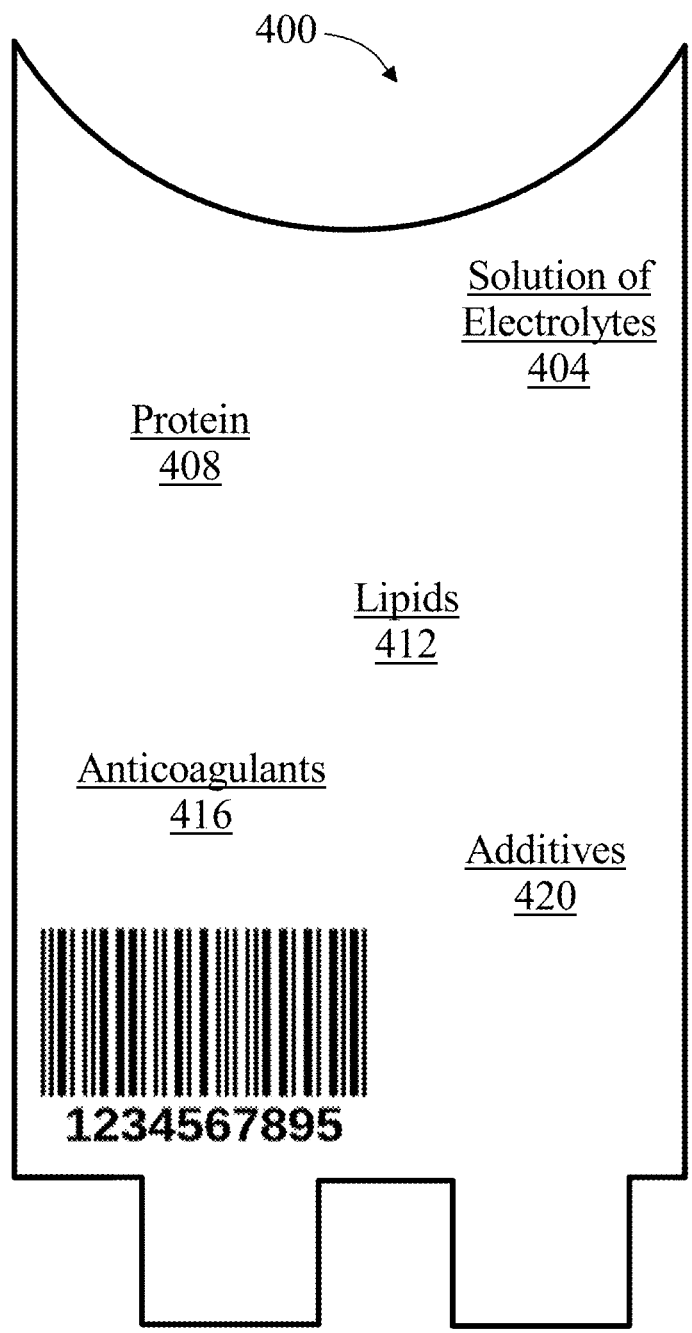
FIG. 4 is a block diagram of an exemplary embodiment of a replacement therapy treatment.

Now referring to FIG. 4, an exemplary replacement therapy treatment 400 is disclosed. Replacement therapy treatment 400 may include solution of electrolytes 404. In this disclosure, "solution of electrolytes" consists of a liquid or solid phase containing at least one solvent, such as water, and an ionizable substance component, such as salt or acid. Solution of electrolytes 404 may include a mixture including but not limited to one or more micronutrients and/or mineral ions such as sodium chloride, sodium lactate, potassium chloride, calcium chloride, magnesium chloride, calcium gluconate, magnesium chloride, magnesium sulphate, magnesium gluconate, magnesium threonate, zinc sulphate, copper gluconate, copper chloride, copper sulphate and the like. Replacement therapy treatment 400 may include protein 408. As used herein, a "protein" is a large biomolecules and macromolecules that comprise one or more long chains of amino acid residues. The protein may include an albumin. "Albumin" is a simple form of protein that is soluble in water and coagulable by heat. Albumin may be present in an amount between about 30 g/L to about 60 g/L, between about 35 g/L to about 55 g/L, or between about 40 g/L to about 50 g/L. The composition of the replacement therapy treatment may include an amount of albumin at least about 60 g/L or at least about 55 g/L. Protein 408 may be globulins. Examples of globulins include, but not limited to immunoglobulin G (IgG), immunoglobulin M (IgM), immunoglobulin A (IgA), immunoglobulin D (IgD), immunoglobulin E (IgE), and the like. In a non-limiting example, the composition of the replacement therapy treatment may include intravenous immunoglobulin. Non-limiting examples of intravenous immunoglobulin may include, but not limited to immunoglobulin G1 (IgG1), immunoglobulin G2 (IgG2), immunoglobulin G3 (IgG3), immunoglobulin G4 (IgG4), or combinations thereof. A total amount of globulins may include an amount between about 30 g to about 50 g, between about 35 g to about 40 g, or between about 30 g to about 40 g. In an embodiment, one or more globulins may be infused to a patient in a particular order and/or at a specified dose. For example, a patient may receive 20 g of albumin infused. In yet another non-limiting example, a patient may receive an infusion of 20 g of albumin alternated with an infusion of 10 g IVIG 5%. In yet another non-limiting example, the composition of the replacement therapy treatment may include an number of globulins at least about 1 g/L to about 20 g/L. Protein 408 may include one or more ingredients including but not limited to fibrinogen, fresh frozen plasma, and/or fresh plasma derived from one or more donors having specified characteristics such as a particular age, sex, disease history, infectious disease history, and the like. Fibrinogen may be present in an amount between about 150 mg/dl to about 400 mg/dl, between about 250 mg/dl to about 300 mg/dl, or between about 350 mg/dl to about 400 mg/dl.

Additionally, and with continued reference to FIG. 4, the composition of replacement therapy treatment 400 may include lipid 412. As used in this disclosure, a "lipid" is a macro biomolecule that is soluble in nonpolar solvents. This may include, but not limited to, phospholipid fatty acid such as lysophosphatidylcholine, phosphatidylcholine, phosphatidylethanolamine, phosphatidylinositol, sphingomyelin and the like; fat-soluble vitamins (like vitamins A, D, E, K); a steroid, and the like. A phospholipid may be present in an amount between about 1.0 mg/m L to about 2.0 mg/ml, or between about 1.0 mg/ml to about 2.2, or between about 1.5 mg/ml to about 2.2.

Additionally or alternatively, and still with reference to FIG. 4, the composition for the replacement therapy treatment 400 may include anticoagulant 416. As used herein, an "anticoagulant" is a chemical substance that prevent or reduce coagulation of blood, or in other words, a blood thinner. Examples of anticoagulants 416 may include, but not limited to ethylenediaminetetraacetic acid (EDTA), sodium citrate, citrate dextrose, Heparin, Enoxaparin, Dalteparin, Nadroparin, and the like.

Additionally, or alternatively, and with continued reference to FIG. 4, the composition for replacement therapy treatment 400 may include additives 420. "Additives" include chemical substances added to foods to produce specific desirable effects. For example, additives 420 may include a surfactant. Additives 420 may include a stabilizer. Examples of stabilizer include, but are not limited to, PVP (Povidone), PVA (Polyvinyl alcohol), PEG (Polyethylene glycol), HPMC (Hypromellose), HPC (Hydroxypropyl cellulose), HEC (Hydroxyethyl cellulose), NaCMC (Carboxymethylcellulose sodium), SD (Docusate sodium), SLS (Sodium lauryl sulfate), PEI (Polyethylene imine), TPGS (D-α-tocopheryl polyethylene glycol succinate), PEO (Polyethylene oxide) or PPO (Polypropylene oxide), and combinations thereof.

With continued reference to FIG. 4, the composition for replacement therapy treatment 400 may include one or more additional ingredients. An "additional ingredient" as used in this disclosure may include a supplemental ingredient added to replacement therapy treatment 400. An additional ingredient may include but is not limited to a protein, amino acid, organic acid, bioidentical compound, biosimilar compound, a hormone, a cell-signaling molecule, RNA, DNA, antisense RNA, and/or any other pharmaceutical and/or non-pharmaceutical ingredient.

With continued reference to FIG. 4, the composition for replacement therapy treatment 400 may include one or more vitamins, minerals, and/or additional ingredients. This may include but is not limited to any vitamin, mineral, alpha lipoic acid, NADH, glutathione, ions, resveratrol, Coenzyme Q10, ubiquinol, 1-arginine and/or any ingredient derived from a biological source.

With continued reference to FIG. 4, the composition for the replacement therapy treatment replacement therapy may include stem cells. A "stem cell" as used in this specification, is a cell that has the ability to develop into a specialized cell and replace cells or tissue that has been damaged. Stem cells may be adult stem cells. "Adult stem cells" as used in this disclosure are stem cells obtained for certain regions of the adult body such as, but not limited to, the epidermis of the skin, the lining of the small intestine, the bone marrow, and the like. Stem cells may be pluripotent. A "pluripotent stem cell" as used in this disclosure, is a stem cell that has the ability to undergo self-renewal and to give rise to all cells of the tissues in the body. A stem cell may include an exosome. An "exosome," as used in this disclosure, is an extracellular vesicle produced in an endosomal compartment of a eukaryotic cell. A stem cell may include a very small embryonic like stem cell (VSEL). In an embodiment, a stem cell may be produced and/or generated using 3-D printing technology.

Figure 5:
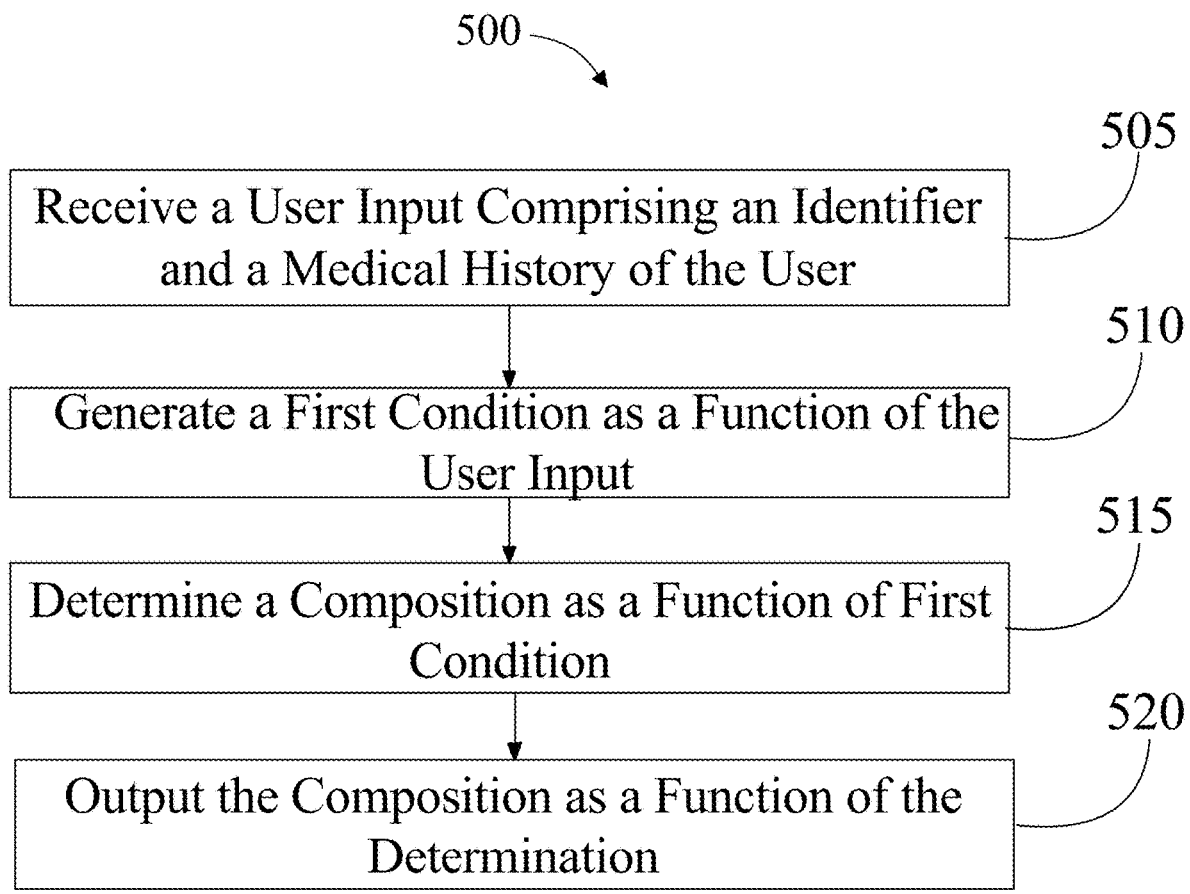
FIG. 5 is a flow diagram illustrating an exemplary embodiment of a method for determining a composition of a replacement therapy treatment.

Now referring to FIG. 5, a flow diagram illustrating an exemplary embodiment of a method 500 for determining a composition of a replacement therapy treatment is illustrated. Method 500 may be performed by a computing device 104. Composition 124 may be any of the compositions described herein with reference to FIGS. 1 and 2. Computing device 104 may be any of the computing devices described herein with reference to FIGS. 1 and 6.

Still referring to FIG. 5, at step 505, method 500 includes receiving, at a computing device 104, a user input 108 wherein user input 108 comprises at least an identifier and a constitutional history of the user. User input 108 may be received by a user device 112. Computing device 104 may be any of the computing devices described herein with reference to FIGS. 1 and 6. User input 108 may be any of the inputs described herein with reference to FIGS. 1 and 2. User device 112 may be any of the devices described herein with reference to FIG. 1.

Still referring to FIG. 5, at step 510, method 500 includes generating, at computing device 104, a first condition descriptor 116 as a function of user input 108. Generating the first condition descriptor comprises identifying a plurality of biomarkers as a function of the user input, calculating a value for each biomarker of the plurality of biomarkers in a biological sample, training a second machine-learning process using a reference biomarker training data wherein the reference biomarker training data correlates reference values for each biomarker to the first conditions, and determining the first condition descriptor as a function of the value for each biomarker of the plurality of biomarkers and the second machine learning process. Generating the first condition descriptor further comprises regenerate, iteratively, the reference biomarker training data as a function of the first condition descriptor and retrain the second machine-learning process using regenerated biomarker training data. Plurality of biomarkers comprise at least a diagnostic biomarker. Computing device 104 may be any of the computing devices described herein with reference to FIGS. 1 and 6. First condition descriptor 116 may be an of the conditions described herein with reference to FIG. 1. User input 108 may be any of the inputs described herein with reference to FIGS. 1 and 2.

Still referring to FIG. 5, at step 515, method 500 includes determining, at a computing device 104, a composition 124 of a replacement therapy treatment as a function of the first condition descriptor 116. Composition 124 of the replacement therapy treatment comprises albumin. Albumin is present in an amount ranging from at least about 30 grams per liter to about 60 grams per liter. Computing device 104 may be any of the computing devices described herein with reference to FIGS. 1 and 6. Composition 124 may be any of the compositions described herein with reference to FIGS. 1 and 2. First condition descriptor 116 may be an of the conditions described herein with reference to FIG. 1.

Still referring to FIG. 5, at step 520, method 500 includes outputting, at a computing device 104, composition 124 of the replacement therapy treatment as a function of the determination. composition of the replacement therapy treatment comprises a solution of electrolytes. composition of the replacement therapy treatment comprises lipids. Computing device 104 may be any of the computing devices described herein with reference to FIGS. 1 and 6. Composition 124 may be any of the compositions described herein with reference to FIGS. 1 and 2.

Still referring to FIG. 5, method 500 may further comprise a robot designed and configured to prepare the composition of the replacement therapy treatment for a user. Robot may be any of the robots designed herein with reference to FIG. 1. Composition 124 may be any of the compositions described herein with reference to FIGS. 1 and 2.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
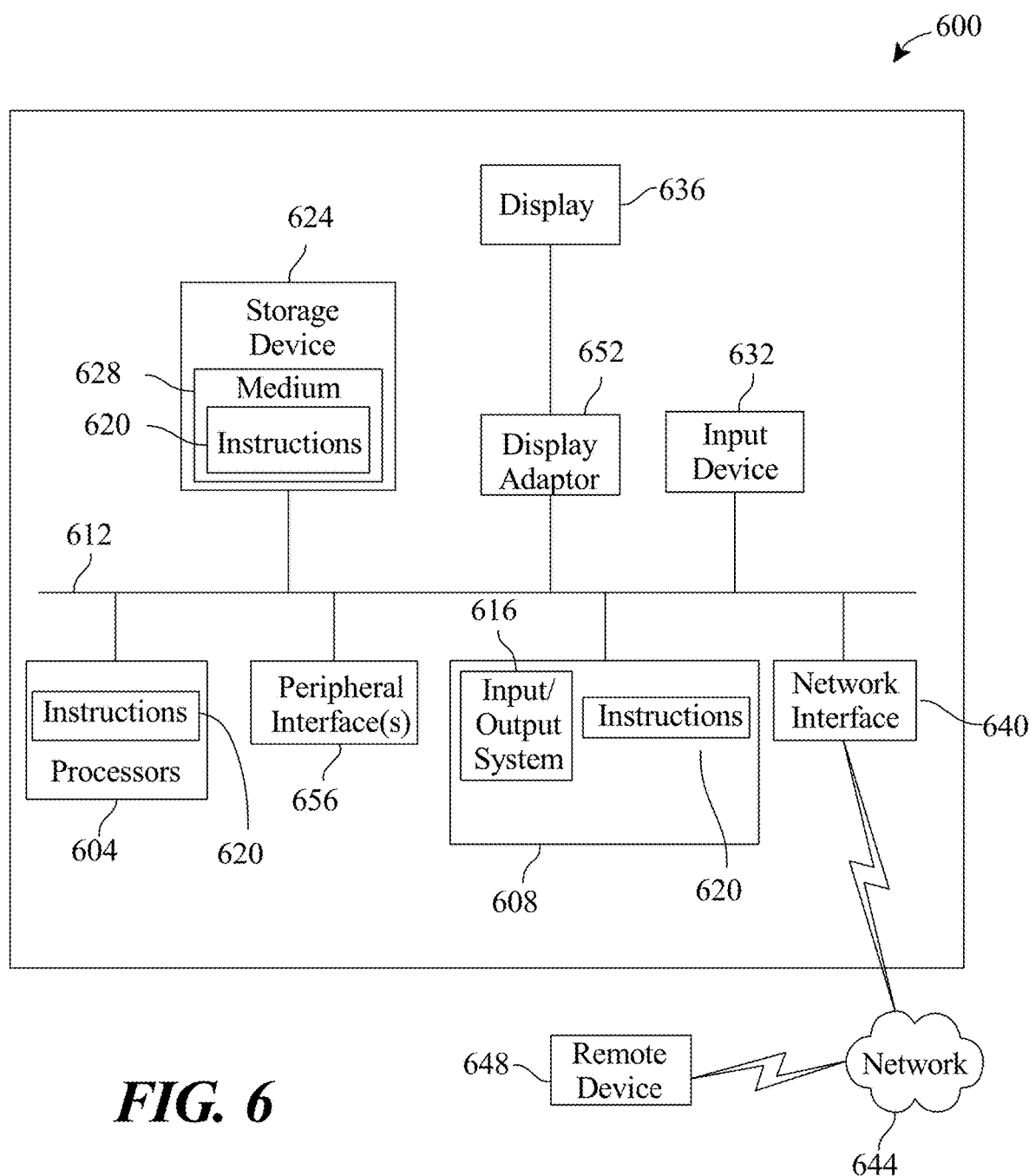
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods and systems, according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for determining a composition of a replacement therapy treatment, the apparatus comprising:
   at least a processor; and
   a memory communicatively connected to the processor, the memory containing instructions configuring the at least a processor to:
      receive a user input, wherein the user input comprises at least an identifier and a constitutional history of the user;
      generate a first condition descriptor as a function of the user input, wherein the first condition descriptor comprises at least a monitoring biomarker configured to monitor the effects of a therapeutic agent and at least a predictive biomarker configured to predict if user will respond favorably to the therapeutic agent;
      determine a composition of a replacement therapy treatment as a function of the first condition descriptor, wherein determining comprises:
         training a first machine-learning process using user training data, wherein the user training data correlates user input data to exemplary compositions of replacement therapy treatment, wherein user training data is configured to convert a data entry into an extensible markup language (XML); and
         determining the composition as a function of the user input using the first machine learning process; and
      output the composition of the replacement therapy treatment as a function of the determination; and
   a robot designed and configured to prepare the composition of the replacement therapy treatment for a user.

2. The apparatus of claim 1, further comprising a database to retrieve the user input from.

3. The apparatus of claim 1, wherein generating the first condition descriptor further comprises:
   identifying a plurality of biomarkers as a function of the user input;
   calculating a value for each biomarker of the plurality of biomarkers in a biological sample;
   training a second machine-learning process using a reference biomarker training data, wherein the reference biomarker training data correlates reference values for each biomarker to condition data; and
   determining the first condition descriptor as a function of the value for each biomarker using the second machine learning process.

4. The apparatus of claim 3, wherein generating the first condition descriptor further comprises:
   regenerate, iteratively, the reference biomarker training data as a function of the first condition; and
   retrain the second machine-learning process using regenerated biomarker training data.

5. The apparatus of claim 3, wherein the plurality of biomarkers comprise at least a diagnostic biomarker.

6. The apparatus of claim 1, wherein the composition of the replacement therapy treatment comprises albumin in an amount ranging from at least 30 grams per liter to 60 grams per liter.

7. The apparatus of claim 1, wherein the composition of the replacement therapy treatment comprises at least an immunoglobulin present in an amount ranging from 0.01 g/liter to 20 g/liter.

8. The apparatus of claim 1, wherein the composition of the replacement therapy treatment comprises a solution of electrolytes.

9. The apparatus of claim 1, wherein the composition of the replacement therapy treatment comprises lipids.

10. A method for determining a composition of a replacement therapy treatment, the method comprises:
    receiving, at a processor, a user input, wherein the user input comprises at least an identifier and a constitutional history of the user;
    generating, at the processor, a first condition descriptor as a function of the user input, wherein the first condition descriptor comprises at least a monitoring biomarker configured to monitor the effects of a therapeutic agent and at least a predictive biomarker configured to predict if user will respond favorably to the therapeutic agent;
    determining, at a processor, a composition of a replacement therapy treatment as a function of the first condition, wherein the determination comprises:
       training a first machine-learning process using user training data, wherein the user training data correlates user inputs to compositions of the replacement therapy treatment, wherein user training data is configured to convert a data entry into an extensible markup language (XML); and
       determining the composition as a function of the user input using the first machine learning process; and
    outputting, at a processor, the composition of the replacement therapy treatment as a function of the determination; and
    preparing, by a robot, the composition of the replacement therapy treatment for a user.

11. The method of claim 10, further comprising a database to retrieve the user input from.

12. The method of claim 10, wherein generating the first condition descriptor further comprises:
    identifying a plurality of biomarkers as a function of the user input;
    calculating a value for each biomarker of the plurality of biomarkers in a biological sample;
    training a second machine-learning process using a reference biomarker training data, wherein the reference biomarker training data correlates reference values for each biomarker to the first conditions; and
    determining the first condition descriptor as a function of the value for each biomarker of the plurality of biomarkers using the second machine learning process.

13. The method of claim 12, wherein generating the first condition descriptor further comprises:
    regenerating, iteratively, the reference biomarker training data as a function of the first condition; and
    retraining the second machine-learning process using regenerated biomarker training data.

14. The method of claim 12, wherein the plurality of biomarkers comprise at least a diagnostic biomarker.

15. The method of claim 10, wherein the composition of the replacement therapy treatment comprises albumin present in an amount ranging from 30 grams to 60 grams.

16. The method of claim 10, wherein the composition of the replacement therapy treatment comprises at least an immunoglobulin present in an amount ranging from 0.01 g/liter to 20 g/liter.

17. The method of claim 10, wherein the composition of the replacement therapy treatment comprises a solution of electrolytes.

18. The method of claim 10, wherein the composition of the replacement therapy treatment comprises lipids.

* * * * *